United States Patent
Uebelacker et al.

(10) Patent No.: US 8,257,282 B2
(45) Date of Patent: Sep. 4, 2012

(54) PRESSURE PULSE/SHOCK WAVE APPARATUS FOR GENERATING WAVES HAVING PLANE, NEARLY PLANE, CONVERGENT OFF TARGET OR DIVERGENT CHARACTERISTICS

(75) Inventors: Walter Uebelacker, Herrsching (DE); Reiner Schultheiss, Illlighausen (CH); Wolfgang Schaden, Vienna (AT); John Warlick, Woodstock, GA (US)

(73) Assignee: General Patent, LLC, Marietta, GA (US)

( * ) Notice: Subject to any disclaimer, the term of this patent is extended or adjusted under 35 U.S.C. 154(b) by 1186 days.

(21) Appl. No.: 11/959,868

(22) Filed: Dec. 19, 2007

(65) Prior Publication Data

US 2008/0146971 A1 Jun. 19, 2008

Related U.S. Application Data

(63) Continuation-in-part of application No. 11/071,156, filed on Mar. 4, 2005, now abandoned.

(60) Provisional application No. 60/621,028, filed on Oct. 22, 2004, provisional application No. 60/642,149, filed on Jan. 10, 2005.

(51) Int. Cl.
*A61H 1/00* (2006.01)
(52) U.S. Cl. ................................. 601/4; 601/2
(58) Field of Classification Search ............ 601/2, 4
See application file for complete search history.

(56) References Cited

U.S. PATENT DOCUMENTS

| | | | |
|---|---|---|---|
| 4,539,989 A | 9/1985 | Forssmann et al. | |
| 4,608,983 A * | 9/1986 | Muller et al. | 601/4 |
| 4,664,111 A | 5/1987 | Reichenberger | |
| 4,702,249 A * | 10/1987 | de la Fonteijne | 601/4 |
| 4,807,627 A | 2/1989 | Eisenmenger | |
| 4,890,603 A | 1/1990 | Filler | |
| 4,905,671 A | 3/1990 | Senge et al. | |
| 5,119,801 A | 6/1992 | Eizenhoefer et al. | |
| 5,143,063 A | 9/1992 | Fellner | |
| 5,174,280 A | 12/1992 | Gruenwald et al. | |
| 5,222,484 A | 6/1993 | Krauss et al. | |
| 5,243,985 A | 9/1993 | Aida et al. | |

(Continued)

FOREIGN PATENT DOCUMENTS

DE 19721218 11/1998

(Continued)

OTHER PUBLICATIONS

Chaussy Ch, Brendel W. Schmiedt E. "Extracorporeally induced destruction of kidney stones by shock waves" Lancet 1980; 2:1265.

(Continued)

*Primary Examiner* — Michael Rozanski
(74) *Attorney, Agent, or Firm* — David L King

(57) ABSTRACT

An apparatus for generating pressure pulse/shock waves (PP/SWs) is disclosed which comprises a pressure pulse/shock wave (PP/SW) source, a housing enclosing said PP/SW source, and an exit window from which wave fronts of waves generated by said PP/SW source emanate. The wave fronts have plane, nearly plane, convergent off target or divergent characteristics. In one embodiment, an extracorporeal shock wave system provides a planar wave for the treatment of tissue. A parabolic reflector is provided in order to propagate the planar wave through a membrane and to the tissue of a human subject. A piezoelectric, electrohydraulic or electromagnetic source may be used to develop the wave.

10 Claims, 9 Drawing Sheets

U.S. PATENT DOCUMENTS

| | | | |
|---|---|---|---|
| 5,305,731 | A | 4/1994 | Buchholtz |
| 5,419,335 | A | 5/1995 | Hartmann |
| 5,545,124 | A | 8/1996 | Krause et al. |
| 5,595,178 | A | 1/1997 | Voss et al. |
| 5,658,239 | A | 8/1997 | Delmenico |
| 5,664,570 | A | 9/1997 | Bishop |
| 5,725,482 | A | 3/1998 | Bishop |
| 6,036,661 | A | 3/2000 | Schwarze et al. |
| 6,068,596 | A | 5/2000 | Weth et al. |
| 6,186,963 | B1 | 2/2001 | Schwarze et al. |
| 6,217,531 | B1 | 4/2001 | Reitmajer |
| 6,368,292 | B1 | 4/2002 | Ogden et al. |
| 6,390,995 | B1 | 5/2002 | Ogden et al. |
| 6,736,784 | B1 | 5/2004 | Menne et al. |
| 6,755,796 | B2 | 6/2004 | Spector |
| 2001/0023326 | A1 | 9/2001 | Spector |
| 2002/0002345 | A1 | 1/2002 | Marlinghaus |
| 2002/0058890 | A1 | 5/2002 | Visuri et al. |
| 2004/0006288 | A1 | 1/2004 | Spector |
| 2004/0010211 | A1 | 1/2004 | Spector |
| 2004/0059265 | A1 | 3/2004 | Candy et al. |
| 2004/0162508 | A1 | 8/2004 | Uebelacker |
| 2005/0010140 | A1 | 1/2005 | Forssmann |
| 2005/0038362 | A1 | 2/2005 | Schultheiss |
| 2005/0075587 | A1 | 4/2005 | Vago et al. |
| 2005/0113722 | A1 | 5/2005 | Schultheiss |
| 2006/0036196 | A1 | 2/2006 | Schaden et al. |

FOREIGN PATENT DOCUMENTS

| | | |
|---|---|---|
| DE | 10065450 | 7/2002 |
| DE | 10304435 | 7/2004 |
| DE | 10311659 | 9/2004 |

OTHER PUBLICATIONS

Wilbert, D.M.; A comparative review of extracorporeal shock wave generation; BJU International, vol. 90, No. 5, Sep. 2002, pp. 507-511(5); Blackwell Publishing.

Meirer, R. et al; Extracorporal shock wave may enhance skin flap survival in an animal model; British Journal of Plastic Surgery; vol. 58, issue 1, Jan 2005, pp. 53-57; copyright 2004; The British Association of Plastic Surgeons, published by Elsevier.

Nishida, T. et al; Extraporeal Cardiac Shock Wave Therapy Markedly Ameliorates Ischemia-Induced Myocardial Dysfunction in Pigs in Vivo; Circulation; Nov. 9, 2004; Circulation 2004; 110; pp. 3055-3061.

Gerdesmeyer, L. et al; Antibacterial Effects of Extracorporeal Shock WAves; World Fed for Ultrasound in Medicine & Biology; printed USA, Elsevier, vol. 31 No. 1, pp. 115-119, 2005.

Haupt, G. et al; Effect of Shock Waves on the Healing of Partial-Thickness Wounds in Piglets; Journal of Surgical Research, vol. 49, No. 1, pp. 45-48, Jul. 1990; Copyright 1990 by Academic Press Inc.

Jagadeesh, G., et al; "Novel applications of micro-shock waves in biological sciences"; J.Indian Inst. Sci. 2002, 82, pp. 1-10.

Theil, M. et al; "The use of shock waves in medicine-a tool of the modern OR; an overview of basic phyusical principles, history and research", Min Invas Ther & Allied Technol; 2000; 9(3/4) 247-253.

\* cited by examiner

PRESSURE PULSE/SHOCK WAVE APPARATUS FOR GENERATING WAVES HAVING PLANE, NEARLY PLANE, CONVERGENT OFF TARGET OR DIVERGENT CHARACTERISTICS

RELATED APPLICATIONS

This application is a continuation in part of U.S. application Ser. No. 11/071,156, filed Mar. 4, 2005 now abandoned entitled "Pressure Pulse/Shock Wave Apparatus for Generating Waves Having Nearly Plane or Divergent Characteristics" and co-pending U.S. application Ser. No. 10/708,249 filed Feb. 19, 2004 entitled "Shock Wave Therapy Method and Device" and co-pending U.S. patent application Ser. No. 11/122,154, filed May 4, 2005 now U.S. Pat. No. 7,470,240 entitled "Pressure Pulse/Shock Wave Therapy Methods and an Apparatus for Conducting the Therapeutic Methods", the disclosures of which are incorporated herein by reference in their entirety.

FIELD OF THE INVENTION

The invention relates to an apparatus which generates acoustical pressure pulse/shock waves having wave fronts with plane, nearly plane, convergent off target or divergent characteristics for applications in human and veterinary medicine.

BACKGROUND OF THE INVENTION

The present application relates to extracorporeal shock wave technology and in particular, an electromagnetic, electrohydraulic or piezoelectric shock wave device that propagates planar waves, and to methods of using such a device, for developing shock waves and for treating tissue.

Shock waves are used in different medical disciplines and in different species. Although it is not known exactly how specific tissue responds to the shock wave, it is proven that shock waves can have a therapeutic effect and improve certain medical conditions.

In urology, the shock wave is used to disintegrate kidney or urethra stones. In orthopedics, shock waves are used to stimulate bone growth in non-unions. Shock wave therapy is further used to treat epicondylitis, tendonitis calcarea of the shoulder, achillodynia calcaneal spurs, and many other conditions. Shock waves are also used in veterinary medicine to treat ligaments, tendons, splint bone fractures, navicular syndrome, back pain, and certain joint conditions.

Commercially available devices use either high-energy focused shock wave systems or radial emitting pressure pulse systems. In these systems the shock wave is generated either by an electrical discharge in a liquid (electro hydraulic), electrical discharge in an electrical coil that drives a diaphragm (electro magnetic), electrical discharge in piezo elements (piezo electric) or a projectile that hits its target (ballistic system).

Focused shock wave systems have an advantage over radial systems because the shock wave reaches its maximal density inside the body. This allows for the treatment of deeper tissue inside the body. Typical penetration depths in orthopedic devices are 100 mm in human medicine or up to 80 mm in veterinary medicine.

Radial systems can only treat superficial conditions because the diverging wave loses energy density with the square of the distance to the source, leading to insufficient energy density to show an effect on deeper tissue inside the body.

Investigations have shown that, for a tissue to respond, the shock wave must reach a certain energy density measured in mJ/mm.sup.2 (milli Joules per square millimeter).

Also the volume of the treated tissue (or area for rather two-dimensional treatment regions, such as tendons) plays an important factor. Treatment results show that these two factors have the major influence on the clinical outcome.

Focused systems have enough energy density in deeper regions but the treatment area is often too small. Either the shock wave source or the patient must be moved to treat a bigger area.

Radial systems treat a bigger area, but the power density is too small to show an effect in deeper tissues.

Electro-hydraulic shock wave systems have been used to disintegrate kidney and urethral stones by applying focused shock waves to the stone. A few hundred up to a few thousand shock waves may be required to break a stone within a mammal into small pieces of 3-4 mm diameter which are able to pass over a period of several weeks through the urethra and the bladder out of the patient's body.

Devices using electro-hydraulic (U.S. Pat. No. 4,539,989), piezoceramic (U.S. Pat. No. 5,119,801) or electromagnetic (U.S. Pat. No. 5,174,280) shock wave or pressure pulse generating elements have been described.

The patents used herein to illustrate the invention and, in particular, to provide additional details respecting the practice are incorporated herein by reference in their entirety.

In certain of non-urological applications, shock waves and pressure pulses may be used to treat/cure orthopedic painful conditions. The treated indications may be related to tendons, ligaments, soft tissue and include muscle pain and calcification in tissue. Suitable devices and procedures have been described (U.S. Pat. Nos. 5,545,124 and 5,595,178). The treatment of tissue with shock waves has also been discussed (United States Patent Application 20040162508).

In certain non-urological applications, shock waves are used to treat ischemic heart tissue for generating better blood supply in the treated tissue and thus recover the tissue's functionality.

Known devices generally make use of more or less strong focused shock waves which are focused by ellipsoidal reflectors in electro-hydraulic devices (U.S. Pat. No. 4,539,989) or by parabolic reflectors in devices using electromagnetic sources which are emitting waves from a cylindrical surface (U.S. Pat. No. 5,174,280). Other electromagnetic sources may make use of acoustic lenses of different shapes, for example, concave or convex, depending on the sound velocity and density of the lens material used (U.S. Pat. No. 5,419,335 and European Patent 1 445 758 A2). Piezoelectric sources often use spherical surfaces to emit acoustic pressure waves which are self focused to the center of the sphere (U.S. Pat. No. 5,222,484). The same type of focusing has been used in spherical electromagnetic devices (U.S. Pat. No. 4,807,627).

There is a need for an apparatus and a process for optimized electro-hydraulic pressure pulse generation by changing the focusing characteristics of a pressure pulse or shock wave so that unfocused wave fronts with plane or nearly plane acoustic wave front and/or convergent off target or divergent acoustic wave front characteristics can be released by the apparatus. As used herein, convergent off target is where the focal region or point is moved away from the treated tissue.

There is also a need for an apparatus for optimized pressure pulse/shock wave generation, wherein waves with defined wave front characteristics, like focused and/or plane, nearly plane, convergent off target and/or divergent are released from the apparatus for treating tissues, in particular, for treating soft tissue, skin or skin near conditions including, but not limited to, skin and skin near conditions caused by trauma or diseases.

There is also a need for providing an apparatus that allows treatment without requiring extensive scanning of the area to be treated. This is usually required to cover an area uniformly if apparatuses using a small focal point are used. Such an apparatus would reduce treatment times.

There is a need for an apparatus that produces waves having plane, nearly plane, convergent off target or divergent acoustic wave front characteristics with adjustably reducible or reduced energy densities compared to wave fronts emitted by focused shock wave generators.

There is also a need for an apparatus and method that allows using existing pressure pulse generating devices to treat tissues which have more area like than volume like characteristics, such as skin.

The task of the present invention is to optimize the interaction of the shock wave with the tissue of a subject being treated so as to achieve the best clinical result. This task is accomplished by using high-energy shock waves that are generated by electro hydraulic, electro magnetic, or piezo-electric means, but not focused into a focal point. Instead, the shock wave is reflected or refracted in such a way that a "plane wave" or "flat wave" is emitted from the source.

With a "plane" or "flat" wave, the energy is neither converging (as with the focused shock wave) or diverging (as with a radial wave). Rather the energy distribution over the emitting area stays the same even in different distances along the axis of the shock wave source. The initial shock wave energy must be enough to reach a certain energy density at the distal end of the shock wave source.

SUMMARY OF THE INVENTION

The present invention provides for an apparatus for generating pressure pulse/shock waves comprising: a pressure pulse/shock wave (PP/SW) source, a housing enclosing said PP/SW source, and an exit window from which wave fronts of waves generated by said PP/SW source emanate, wherein said wave fronts have plane, nearly plane, convergent off target or divergent characteristics.

The PP/SW source may comprise a pressure pulse/shock wave generating element for generating pressure pulses/ shock waves, a focusing element for focusing the waves into a focus volume outside the focusing element. The apparatus may further comprise a movable elongated mechanical element having a longitudinal axis, wherein said focus volume is situated on or at said longitudinal axis, and said movable elongated mechanical element is movable to extend to or beyond said focus volume so that wave fronts with divergent characteristics emanate from said exit window. The movable elongated element may be part of the housing and the exit window may be a window of the housing. The focusing element may be an acoustic lens, a reflector or a combination thereof.

The PP/SW source may also comprise a pressure pulse/ shock wave generating element and waves emanate from the exit window of the housing without being focused by a focusing element.

The PP/SW source may also comprise an electro-hydraulic pressure pulse/shock wave generating element. The element may comprise at least two electrodes. In this case, the PP/SW source may also comprise a generalized paraboloid according to the formula $y''=2px$, wherein x and y are carthesian coordinates, p/2 is a focal point measured from an apex of the generalized paraboloid, and n is about $1.2<2$ or $2<$ about 2.8, with $n\neq 2$.

The electrodes may be positioned within the generalized paraboloid, and a spark between tips of said electrodes may be, with about +/−5 mm of variance, generated at the focal point p/2 of the generalized paraboloid. The burn down of the electrode tips (z) may be compensated by the selection of (p+/−z) and n so that the resulting generalized paraboloid has a configuration between a paraboloid defined by formula $y^2=2(p+z)x$ and a paraboloid defined by formula $y^2=2(p-z)x$.

The PP/SW source may also comprise an electromagnetic pressure pulse/shock wave generating element. The electromagnetic pressure pulse/shock wave generating element may be an electromagnetic flat or curved emitter emitting waves having nearly plane or divergent characteristics, and wherein the waves emanate from said exit window without being further modified by a lens. The electromagnetic pressure pulse/shock wave generating element may also be an electromagnetic flat emitter emitting waves having nearly plane characteristics. Here, the PP/SW source may further comprise a lens for focusing said waves in a first focal point, wherein divergent waves generated behind said focal point and emanate from the exit window. The PP/SW source may alternatively comprise at least one lens for de-focusing said waves so that waves with divergent wave characteristics emanate from the exit window.

The electromagnetic pressure pulse/shock wave generating element may also be an electromagnetic cylindrical emitter. Here, the PP/SW source may further comprise at least one reflecting element and/or at least one lens.

The PP/SW source may also comprise a piezoceramic pressure pulse/shock wave generating element. The piezoceramic pressure pulse/shock wave generating element may be a piezoceramic flat or curved emitter generating waves having nearly plane or divergent characteristics, and wherein said waves emanate from said exit window without being modified by a lens. The curved emitter may have a curved piezoceramic emitting surface generating waves having divergent characteristics. The piezoceramic pressure pulse/shock wave generating element may also be a piezoceramic flat emitter for emitting waves having nearly plane characteristics. Here, the PP/SW source may further comprise a lens for focusing said waves in a first focal point, wherein divergent waves generated behind said first focal point emanate at said exit window. The PP/SW source may alternatively further comprise at least one lens for de-focusing said waves into divergent waves so that waves with divergent wave characteristics emanate from the exit window.

The piezoceramic pressure pulse/shock wave generating element may also be a piezoceramic cylindrical emitter. Here, the PP/SW source may further comprise at least one reflecting element and/or at least one lens.

The present invention pertains to a shock wave device comprising a reflector housing, a parabolic reflector disposed in the housing, and an energy source disposed within the reflector for developing a shock wave so that a planar shock wave is formed by the reflector and emanates from the housing. In an embodiment, the reflector is shaped and dimensioned to provide a reflected wave having a power density level to produce a tissue reaction in a subject to which the wave is administered. In an embodiment, the power density may be in the range of approximately 0.01 mJ/mm.sup.2 to 1.0 mJ/mm.sup.2. In an embodiment, the opening of the paraboloid may have a diameter in the range of approximately 20 mm to 100 mm. In an embodiment, the distance between the origin point of the paraboloid to a propagation point may be in the range of approximately 3 mm to 10 mm.

In an embodiment, the energy source may be an electro hydraulic source. In an embodiment, the energy source may have a propagation point centered approximately at the focal point of the parabolic reflector. In an embodiment, the energy source may comprise a pair of electrode tips connected to a capacitor. In an embodiment, the energy source may have a propagation point centered approximately between the electrode tips. In an embodiment, the reflector may include a cavity having an opening sealed by a membrane. In an embodiment, the cavity may contain a fluid. In an embodiment, the fluid may be water.

An embodiment of the invention may provide for a method for developing a planar shock wave to be used for therapeutic purposes on a subject, the method comprising the steps of generating a spark to cause a shock wave, shaping and directing the shock wave to create a planar wave and propagating the planar shock wave toward the subject. In an embodiment, the method may further comprise the steps of providing a device having a parabolic reflector, an energy source attached to an electrode tip and a membrane disposed across a cavity in communication with the parabolic reflector, orienting the electrode tip at a focal point of the parabolic reflector, generating a spark at the electrode tip and developing a shock wave, propagating the shock wave so that it reflects at the parabolic reflector, forming a planar wave, propagating the planar wave through the membrane and toward tissue of a subject to receive the planar wave for therapeutic effect.

An embodiment of the invention provides a method for treating tissue comprising the steps of generating a planar shock wave and coupling the planar shock wave to the tissue to be treated. In an embodiment, the method may further comprise the steps of providing a treatment device that develops a shock wave, orienting the treatment device adjacent to the tissue area, forming a planar shock wave to be propagated from the treatment device and to be dispersed through the tissue and activating the tissue in order to cause a chemical release from the tissue cells. In an embodiment, the shockwave may be developed by electro hydraulic, electromagnetic or piezoelectric means. In an embodiment, the method may comprise the steps of generating a spark by an electrode tip to develop the shockwave and reflecting the shockwave from a parabolic reflector. In an embodiment, the tissue is activated to release a protein for generating an immune response.

An embodiment of the invention provides for a therapeutic device for administering a shock wave to a subject comprising a housing, a shock wave source disposed in the housing, wave directing and shaping structure in the housing responsive to the shock wave for causing a planar shock wave to be emitted from the housing, and structure for coupling the shock wave to the subject. In and embodiment the wave directing and shaping structure includes a parabolic reflector. In an embodiment the housing includes an opening and the coupling structure includes a membrane disposed across the opening. In an embodiment the wave directing and shaping structure is disposed in a cavity having the opening. In an embodiment the shock wave source includes an electrode that develops a spark.

Definitions

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different way, for example: A focused wave will become divergent once it has passed through the focal point. Spherical waves are also included in this definition of divergent waves and have wave fronts with divergent characteristics.

A "generalized paraboloid" according to the present invention is also a three-dimensional bowl. In two dimensions (in Cartesian coordinates, x and y) the formula $y^n=2px$ [with n being $\neq 2$, but being greater than about 1.2 and smaller than 2, or greater than 2 but smaller than about 2.8]. In a generalized paraboloid, the characteristics of the wave fronts created by electrodes located within the generalized paraboloid may be corrected by the selection of (p (−z,+z)), with z being a measure for the burn down of an electrode, and n, so that phenomena including, but not limited to, burn down of the tip of an electrode (−z,+z) and/or disturbances caused by diffraction at the aperture of the paraboloid are compensated for.

"Nearly plane waves" also do not have a focus to which their fronts move (focused) or from which the fronts are emitted (divergent). The amplitude of their wave fronts (having "nearly plane" characteristics) are approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "paraboloid" according to the present invention is a three-dimensional reflecting bowl. In two dimensions (in Cartesian coordinates, x and y) the formula $y^2=2px$, wherein p/2 is the distance of the focal point of the paraboloid from its apex, defines the paraboloid. Rotation of the two-dimensional figure defined by this formula around its longitudinal axis generates a de facto paraboloid.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent).

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milli-seconds (ms). Very fast pressure pulses are called shock waves. Shock waves used in medical applications do have amplitudes above 0.1 MPa and rise times of the amplitude are below 100 ns. The duration of a shock wave is typically below 1-3 micro-seconds (μs) for the positive part of a cycle and typically above some microseconds for the negative part of a cycle.

Waves/wave fronts described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

BRIEF DESCRIPTION OF THE DRAWINGS

For the purpose of facilitating an understanding of the invention, there is illustrated in the accompanying drawings an embodiment thereof, from an inspection of which, when considered in connection with the following description, its construction and operation, and many of its advantages should be readily understood and appreciated.

DETAILED DESCRIPTION OF THE INVENTION

Figure 1:
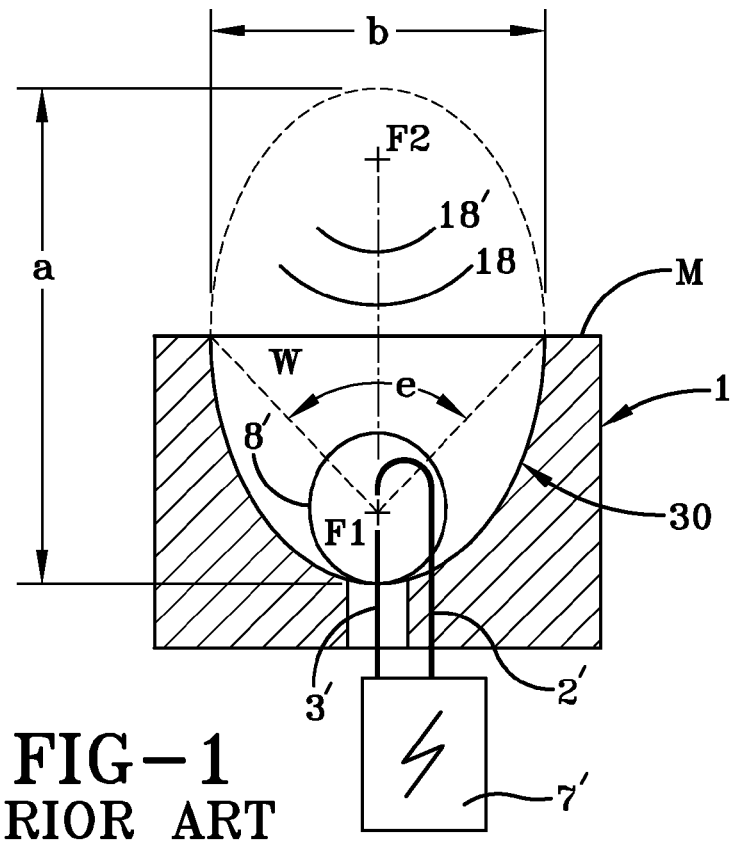
FIG. 1 is a diagrammatic view of a section through a prior art shock wave device propagating a focused wave.

FIG. 1 shows a drawing of a conventional device having a high-voltage generator that stores electrical energy in capacitors. Electrode tips 2' and 3' are electrically connected to the high-voltage unit 7' and are disposed in a housing 1 for a reflector 4'. The housing 1 is filled with a liquid W. In a preferred embodiment, the liquid W is water. To keep the water within the housing, it is sealed by a membrane M. A spark is generated between the two electrode tips 2 and 3 which are centered at the focal point F1 of the ellipsoid, to generate a shock wave 8. The membrane M provides a contact surface of the device to the treatment area. As the shock wave is expanding it will hit the reflector of an ellipsoidal shape. The inner surface of reflector 4 has an ellipsoid shape to reflect the shock wave, as at 10 and 10", toward focal point F2. The reflected part of the spherical shockwave represented by the space angle e is determined by the cutoff point (M) of the ellipsoid and by the half axes of a and b of the ellipsoid.

Figure 2:
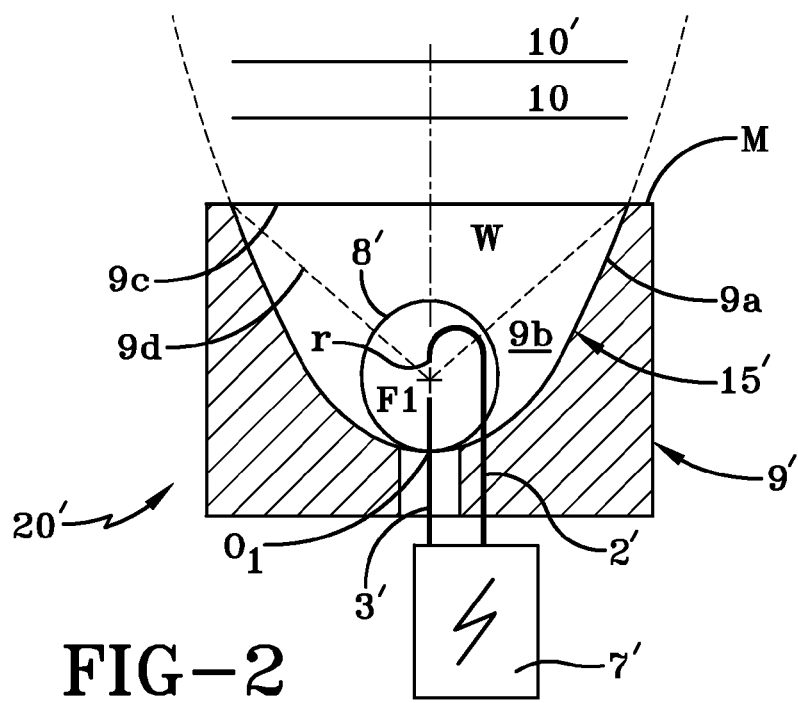
FIG. 2 is a view similar to FIG. 1 of a shock wave device of the present invention propagating a planar wave which emits wave fronts with plane waves as shown in FIG. 1.

FIG. 2 depicts a device 20' of the present invention including the high-voltage generator 7' that stores electrical energy in capacitors and is provided with the electrodes 2' and 3'. The amount of electrical energy is given by the voltage and the capacitance and usually the capacitors are charged to 10 kV to 30 kV, the capacitance being in the range from 10 nF to 50 nF, leading to electrical energy stored in the capacitors in the range of from 0.5 J to 23 J for an electrohydraulic system.

A reflector housing in an embodiment may be made of ceramic, brass, steel, aluminum or other metals. In an embodiment, the housing 9' is cylindrically shaped. In the housing 9' is a reflector 15' which has a parabolic shape (as shown in Fig. In an embodiment, the reflector 15' and housing 9' may be integrally formed. In an alternate embodiment, the reflector 15' may be a separate surface from the housing 9' and a wall 9a of the reflector 15' has a thickness of approximately 3 mm. The reflector housing 9' includes a cavity 9b that is filled with a fluid W that transmits the shockwave. In an embodiment the fluid W is water. To keep the water contained within the cavity 9b, the housing 9' is sealed by a membrane M. In an embodiment, the membrane M consists of soft PVC and its wall thickness is in the range of approximately 1 to 3 mm. PVC has a good acoustic matching to the water so that the reflection losses will be low. The membrane M may also provide a contact surface of the device to the treatment area. To achieve a good acoustic coupling of the shock wave from the device into the treatment area a coupling gel, such as ultra sound gel, may be used.

The device 20' includes a wave directing and shaping structure, such as the reflector wall that is formed having a parabolic shape. Water is contained within the paraboloid The paraboloid has an origin $O_1$ and focal point In a preferred embodiment, the distance between F1 and $O_1$ is approximately 3 mm to 10 mm.

In use, a high-voltage discharge from the capacitor 7' causes a spark to be generated between the electrode tips 3' and 2', which are disposed substantially at the focal point. The spark provides a shock wave source that creates a spherical shock wave illustrated as a circle The wave is illustrated in FIG. 2 prior to reflection. In an electro hydraulic system, the shock wave 8' generates a plasma bubble. The focal point F1 provides a propagation point that is centered between the electrode tips and 3.

As the plasma bubble expands spherically and cools down, it drives a shock wave in front of it. If the expansion velocity of the plasma bubble is lower than the velocity of sound of the surrounding medium W, a spherical shock wave is released and detaches from the expanding plasma bubble. As the wave propagates, its lower portion will reflect against the lower portion of the parabolic reflector and propagate a planar wave that will move through the reflector cavity The planar wave will move toward the opening of the cavity which is defined by the intersection with the membrane M of a conical angle r having its apex at the focal point F1. The wave then propagates through the membrane that couples the shock wave and will propagate it through the skin and tissue of the subject which the membrane is placed against.

The energy density of the shock wave is determined for a given energy by the distance of F1 from the origin point $O_1$ of the paraboloid. The reflected part of the spherical shockwave represented by the space angle r is determined by the cut-off distance (M) of the paraboloid from its focal point. The wave propagates in a way that a flat shock wave 10 and 10' is released from the shock wave device. The wave propagates into the patient as represented by wave and a wave further in time". In a preferred embodiment, the paraboloid has an opening 9c having a diameter which is in the range of approximately 20 mm to 100 mm. In a preferred embodiment, the power density of the wave is in the range of 0.01 mJ/mm$^2$ to 1 mJ/mm$^2$.

In an alternate embodiment, the device 20' may be piezo electric or electromagnetic and provide a wave via means other than the electrohydraulic system depicted in FIG. 2. In such embodiments, a lens may be used in place of the reflector 15'. In a further alternate embodiment, a rod which forms a cylindrical wave source wave may be used. In such an embodiment, the reflector may have side walls forming a conical angle of approximately 45.degree. in order to develop the planar wave.

The above arrangement depicted in FIG. wherein F1 is approximately 3 mm to 10 mm from the origin of the paraboloid, will provide a wave that has a proper power density so that the wave can affect tissues in a human body in order to cause a therapeutic effect. For example, an energy density is high enough to trigger a physiological repair response within the cell. Such mechanisms may include release of cytokines induction of heat, shock, protein and other immunological responses. Such responses may be generated by a planar shock wave of 50 to 1,000 isonorm bars. This planar wave will penetrate deeply into a human subject so that tissue treatments may be helpful through a large area.

These and other beneficial treatments are made possible by using an apparatus with a shock wave emission either singularly or in an array as described below in the embodiments shown in FIGS. 1-12

Figure 1A:
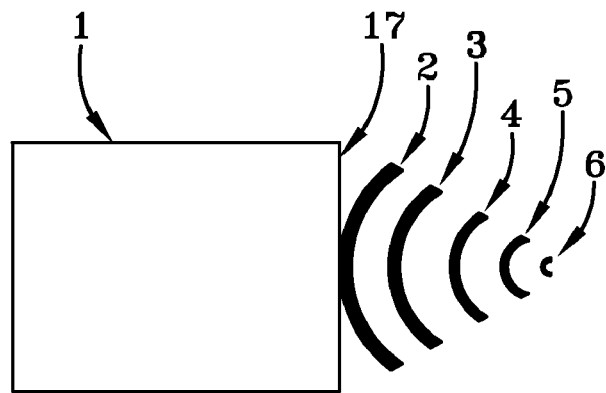
FIG. 1a is a simplified depiction of a pressure pulse/shock wave (PP/SW) generator with focusing wave characteristics.

FIG. 1a is a simplified depiction of the a pressure pulse/shock wave (PP/SW) generator, such as a shock wave head, showing focusing characteristics of transmitted acoustic pressure pulses. Numeral 1 indicates the position of a generalized pressure pulse generator, which generates the pressure pulse and, via a focusing element, focuses it outside the housing to treat diseases. The diseased organ is generally located in or near the focal point which is located in or near position 6. At position 17 a water cushion or any other kind of exit window for the acoustical energy is located.

Figure 1B:
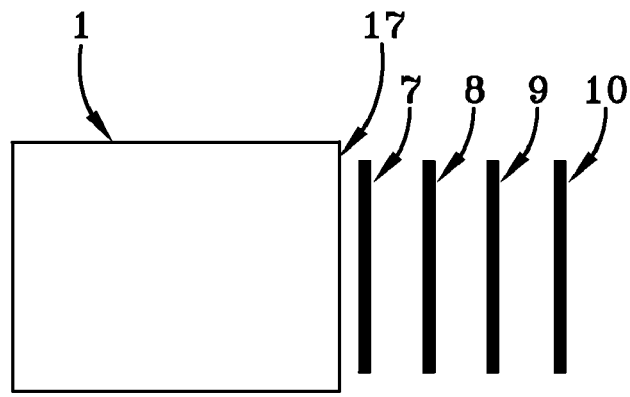
FIG. 1b is a simplified depiction of a pressure pulse/shock wave generator with plane wave characteristics.

FIG. 1b is a simplified depiction of a pressure pulse/shock wave generator, such as a shock wave head, with plane wave characteristics. Numeral 1 indicates the position of a pressure pulse generator according to the present invention, which generates a pressure pulse which is leaving the housing at the position 17, which may be a water cushion or any other kind of exit window. Somewhat even (also referred to herein as "disturbed") wave characteristics can be generated, in case a paraboloid is used as a reflecting element, with a point source (e.g. electrode) that is located in the focal point of the paraboloid. The waves will be transmitted into the patient's body via a coupling media such as, e.g., ultrasound gel or oil and their amplitudes will be attenuated with increasing distance from the exit window 17.

Figure 1C:
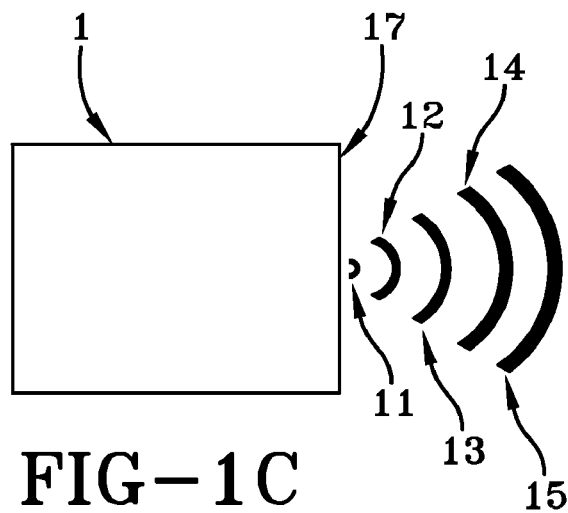
FIG. 1c is a simplified depiction of a pressure pulse/shock wave generator with divergent wave characteristics.

FIG. 1c is a simplified depiction of a pressure pulse shock wave generator (shock wave head) with divergent wave characteristics. The divergent wave fronts may be leaving the exit window 17 at point 11 where the amplitude of the wave front is very high. This point 17 could be regarded as the source point for the pressure pulses. In FIG. 1c the pressure pulse source may be a point source, that is, the pressure pulse may be generated by an electrical discharge of an electrode under water between electrode tips. However, the pressure pulse may also be generated, for example, by an explosion. The divergent characteristics of the wave front may be a consequence of the mechanical setup shown in FIG. 2b.

Figure 2A:
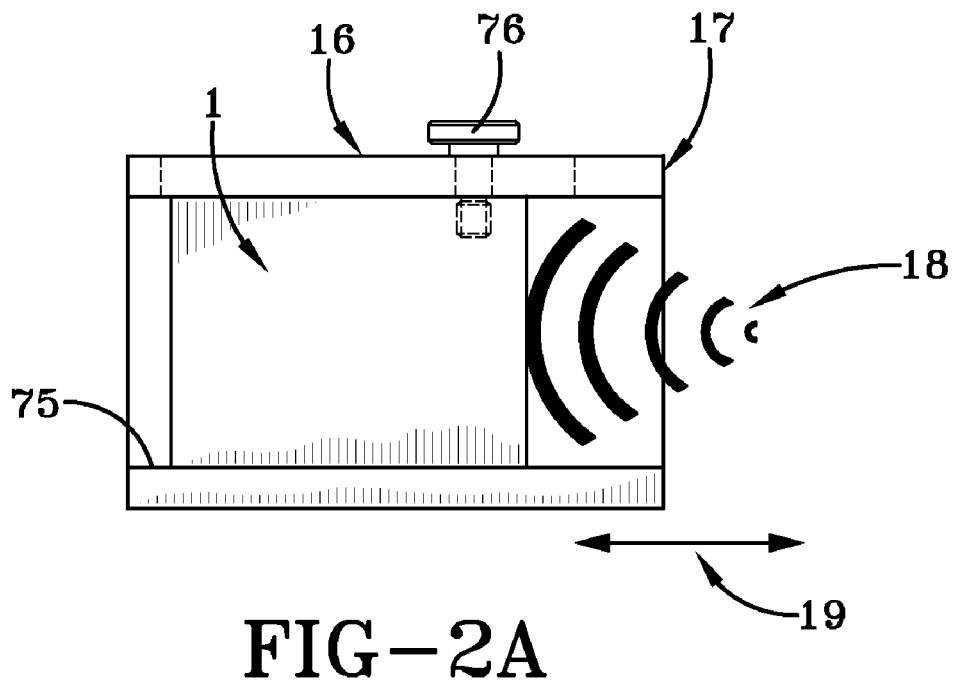
FIG. 2a is a simplified depiction of a pressure pulse/shock wave generator having an adjustable exit window along the pressure wave path. The exit window is shown in a focusing position.

FIG. 2a is a simplified depiction of a pressure pulse/shock wave generator (shock wave head) according to the present invention having an adjustable or exchangeable (collectively referred to herein as "movable") housing around the pressure wave path. The apparatus is shown in a focusing position. FIG. 2a is similar to FIG. 1 a but depicts an outer housing 16 in which the acoustical pathway (pressure wave path) is located. In a preferred embodiment, this pathway is defined by especially treated water (for example, temperature controlled, conductivity and gas content adjusted water) and is within a water cushion or within a housing having a permeable membrane, which is acoustically favorable for the transmission of the acoustical pulses. In certain embodiments, a complete outer housing 16 around the pressure pulse/shock wave generator 1 may be adjusted by moving this housing 16 in relation to, e.g., the focusing element in the generator along a channel or pair of channels 75, sliding to a desired location to fix the location by tightening a thumb screw 76 by way of example. However, as the person skilled in the art will appreciate, this is only one of many embodiments of the present invention. While the figure shows that the exit window 17 may be adjusted by a movement of the complete housing 16 relative to the focusing element, it is clear that a similar, if not the same, effect can be achieved by only moving the exit window, or, in the case of a water cushion, by filling more water in the volume between the focusing element and the cushion. FIG. 2a shows the situation in which the arrangement transmits focused pressure pulses.

Figure 2B:
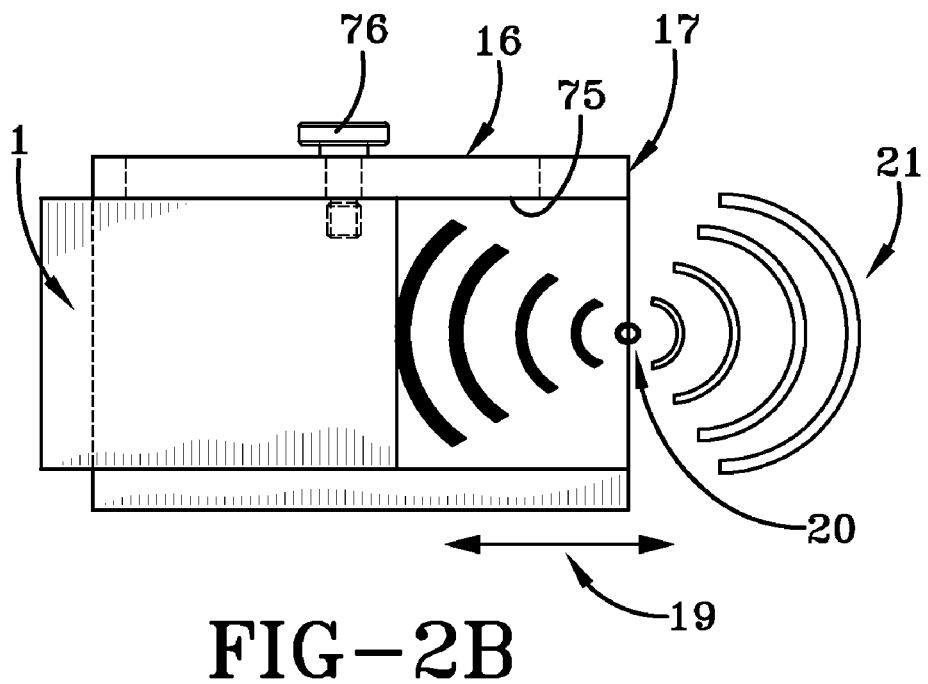
FIG. 2b is a simplified depiction of a pressure pulse/shock wave generator having an exit window along the pressure wave path. The exit window as shown is positioned at the highest energy divergent position.

FIG. 2b is a simplified depiction of the pressure pulse/shock wave generator (shock wave head) having an adjustable or exchangeable housing around the pressure wave path with the exit window 17 being in the highest energy divergent position. The configuration shown in FIG. 2b can, for example, be generated by moving the housing 16 including the exit window 17, or only the exit window 17 of a water cushion, towards the right (as shown in the Figure) to the second focus f2 20 of the acoustic waves. In a preferred embodiment, the energy at the exit window will be maximal. Behind the focal point, the waves may be moving with divergent characteristics 21.

Figure 2C:
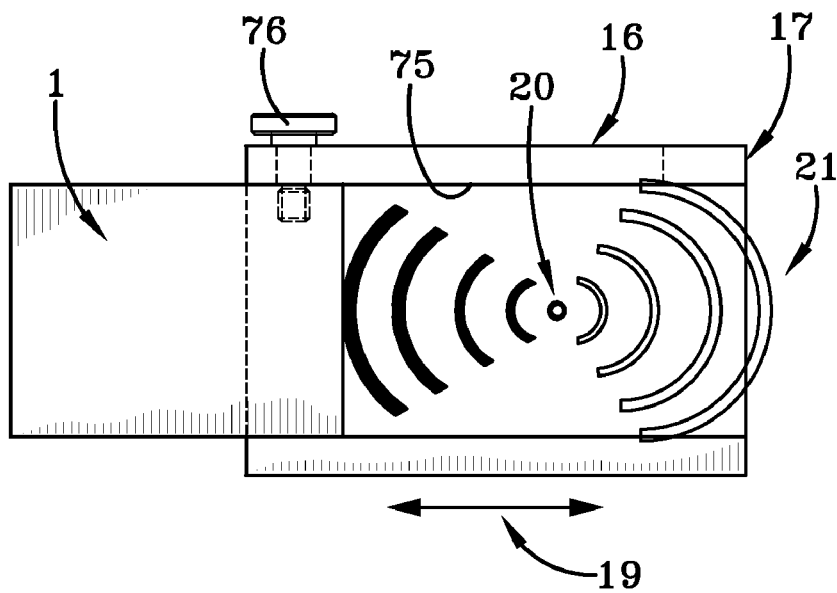
FIG. 2c is a simplified depiction of a pressure pulse/shock wave generator having an exit window along the pressure wave path. The exit window is shown at a low energy divergent position.

FIG. 2c is a simplified depiction of the pressure pulse/shock wave generator (shock wave head) having an adjustable or exchangeable housing around the pressure wave path in a low energy divergent position. The adjustable housing or water cushion is moved or expanded much beyond f2 position 20 so that highly divergent wave fronts with low energy density values are leaving the exit window 17 and may be coupled to a patient's body. Thus, an appropriate adjustment can change the energy density of a wave front without changing its characteristic.

This apparatus may, in certain embodiments, be adjusted/modified/or the complete shock wave head or part of it may be exchanged so that the desired and/or optimal acoustic profile such as one having wave fronts with focused, nearly plane or divergent characteristics can be chosen.

A change of the wave front characteristics may, for example, be achieved by changing the distance of the exit acoustic window relative to the reflector, by changing the reflector geometry, by introducing certain lenses or by removing elements such as lenses that modify the waves produced by a pressure pulse/shock wave generating element. Exemplary pressure pulse/shock wave sources that can, for example, be exchanged for each other to allow an apparatus to generate waves having different wave front characteristics are described in detail below.

In certain embodiments, the change of the distance of the exit acoustic window can be accomplished by a sliding movement. However, in other embodiments of the present invention, in particular, if mechanical complex arrangements, the movement can be an exchange of mechanical elements.

In one embodiment, mechanical elements that are exchanged to achieve a change in wave front characteristics include the primary pressure pulse generating element, the focusing element, the reflecting element, the housing and the membrane. In another embodiment, the mechanical elements further include a closed fluid volume within the housing in which the pressure pulse is formed and transmitted through the exit window.

In one embodiment, the apparatus of the present invention is used in combination therapy. Here, the characteristics of waves emitted by the apparatus are switched from, for example, focused to divergent or from divergent with lower energy density to divergent with higher energy density. Thus, effects of a pressure pulse treatment can be optimized by using waves having different characteristics and/or energy densities, respectively.

While the above described universal toolbox of the present invention provides versatility, the person skilled in the art will appreciate that apparatuses that only produce waves having, for example, nearly plane characteristics, are less mechanically demanding and fulfill the requirements of many users.

As the person skilled in the art will also appreciate that embodiments shown in drawings 1a-1c and 2a-2c are independent of the generation principle and thus are valid for not only electro-hydraulic shock wave generation but also for, but not limited to, PP/SW generation based on electromagnetic, piezoceramic and ballistic principles. The pressure pulse generators may, in certain embodiments, be equipped with a water cushion that houses water which defines the path of pressure pulse waves that is, through which those waves are transmitted. In a preferred embodiment, a patient is coupled via ultrasound gel or oil to the acoustic exit window 17, which can, for example, be an acoustic transparent membrane, a water cushion, a plastic plate or a metal plate.

Figure 3:
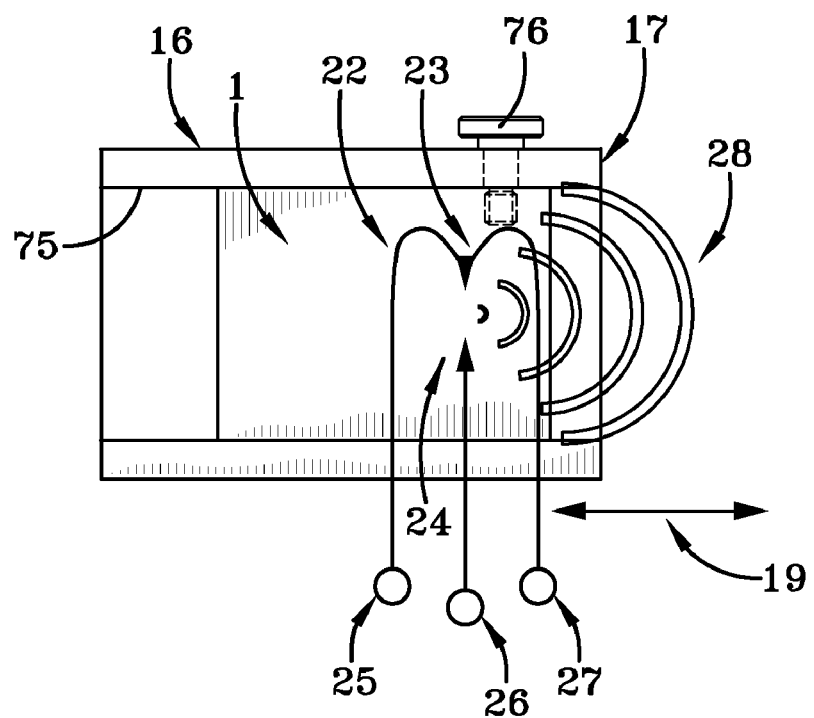
FIG. 3 is a simplified depiction of an electro-hydraulic pressure pulse/shock wave generator having no reflector or focusing element. Thus, the waves of the generator did not pass through a focusing element prior to exiting it.

FIG. 3 is a simplified depiction of the pressure pulse/shock wave apparatus having no focusing reflector or other focusing element. The generated waves emanate from the apparatus without coming into contact with any focusing elements. FIG. 3 shows, as an example, an electrode as a pressure pulse generating element producing divergent waves 28 behind the ignition point defined by a spark between the tips of the electrode 23, 24.

Figure 4A:
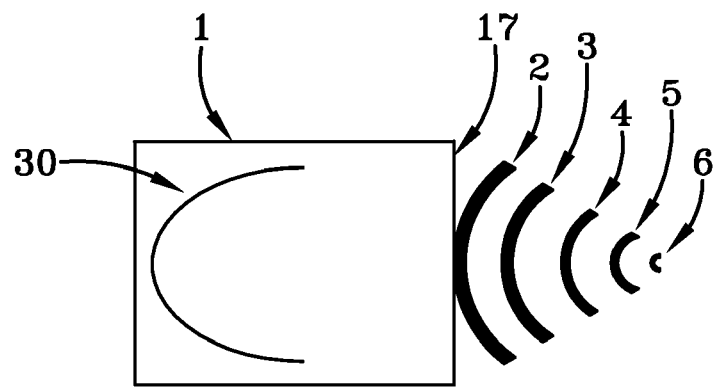
FIG. 4a is a simplified depiction of a pressure pulse/shock wave generator having a focusing element in the form of an ellipsoid. The waves generated are focused.

FIG. 4a is a simplified depiction of the pressure pulse/shock wave generator (shock wave head) having as focusing element an ellipsoid 30. Thus, the generated waves are focused at 6.

Figure 4B:
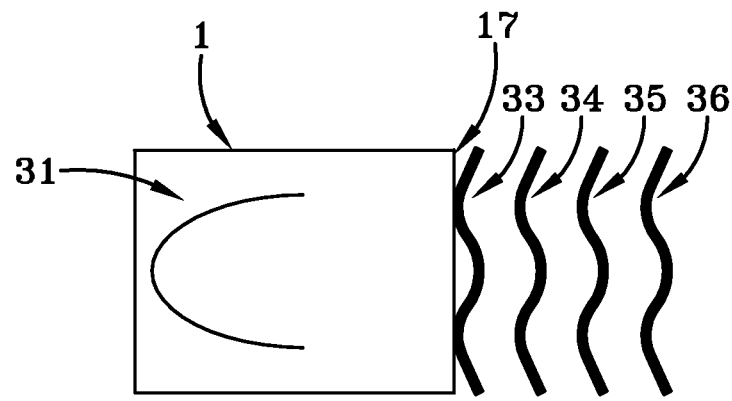
FIG. 4b is a simplified depiction of a pressure pulse/shock wave generator having a parabolic reflector element and generating waves that are disturbed plane.

FIG. 4b is a simplified depiction of the pressure pulse/shock wave generator (shock wave head) having as a focusing element an paraboloid ($y^2=2px$). Thus, the characteristics of the wave fronts generated behind the exit window 33, 34, 35, and 36 are disturbed plane ("parallel"), the disturbance resulting from phenomena ranging from electrode burn down, spark ignition spatial variation to diffraction effects. However, other phenomena might contribute to the disturbance.

Figure 4C:
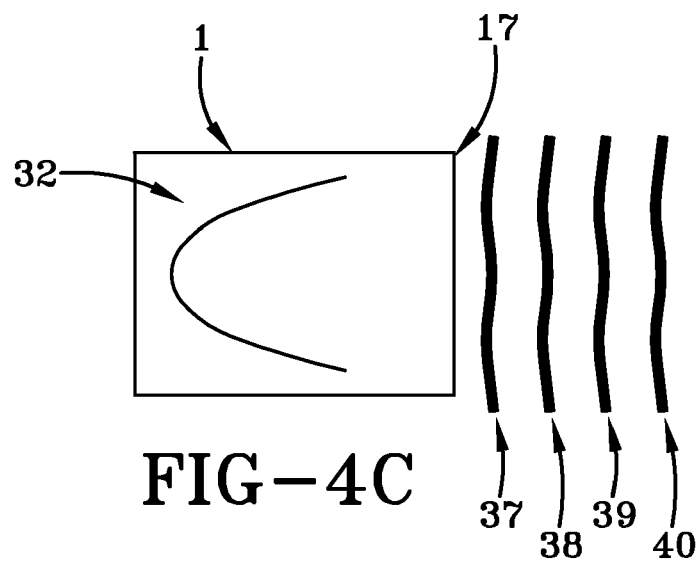
FIG. 4c is a simplified depiction of a pressure pulse/shock wave generator having a quasi parabolic reflector element (generalized paraboloid) and generating waves that are nearly plane/have nearly plane characteristics.

FIG. 4c is a simplified depiction of the pressure pulse/shock wave generator (shock wave head) having as a focusing element a generalized paraboloid ($y^n=2px$, with $1.2<n<2.8$ and $n\neq 2$). Thus, the characteristics of the wave fronts generated behind the exit window 37, 38, 39, and 40 are, compared to the wave fronts generated by a paraboloid ($y^2=2px$), less disturbed, that is, nearly plane (or nearly parallel or nearly even 37, 38, 39, 40). Thus, conformational adjustments of a regular paraboloid ($^2=2px$) to produce a generalized paraboloid can compensate for disturbances from, e.g., electrode burn down. Thus, in a generalized paraboloid, the characteristics of the wave front may be nearly plane due to its ability to compensate for phenomena including, but not limited to, burn down of the tips of the electrode and/or for disturbances caused by diffraction at the aperture of the paraboloid. For example, in a regular paraboloid ($y^2=2px$) with $p=1.25$, introduction of a new electrode may result in p being about 1.05. If an electrode is used that adjusts itself to maintain the distance between the electrode tips ("adjustable electrode") and assuming that the electrodes burn down is 4 mm ($z=4$ mm), p will increase to about 1.45. To compensate for this burn down, and here the change of p, and to generate nearly plane wave fronts over the life span of an electrode, a generalized paraboloid having, for example $n=1.66$ or $n=2.5$ may be used. An adjustable electrode is, for example, disclosed in U.S. Pat. No. 6,217,531.

Figure 4D:
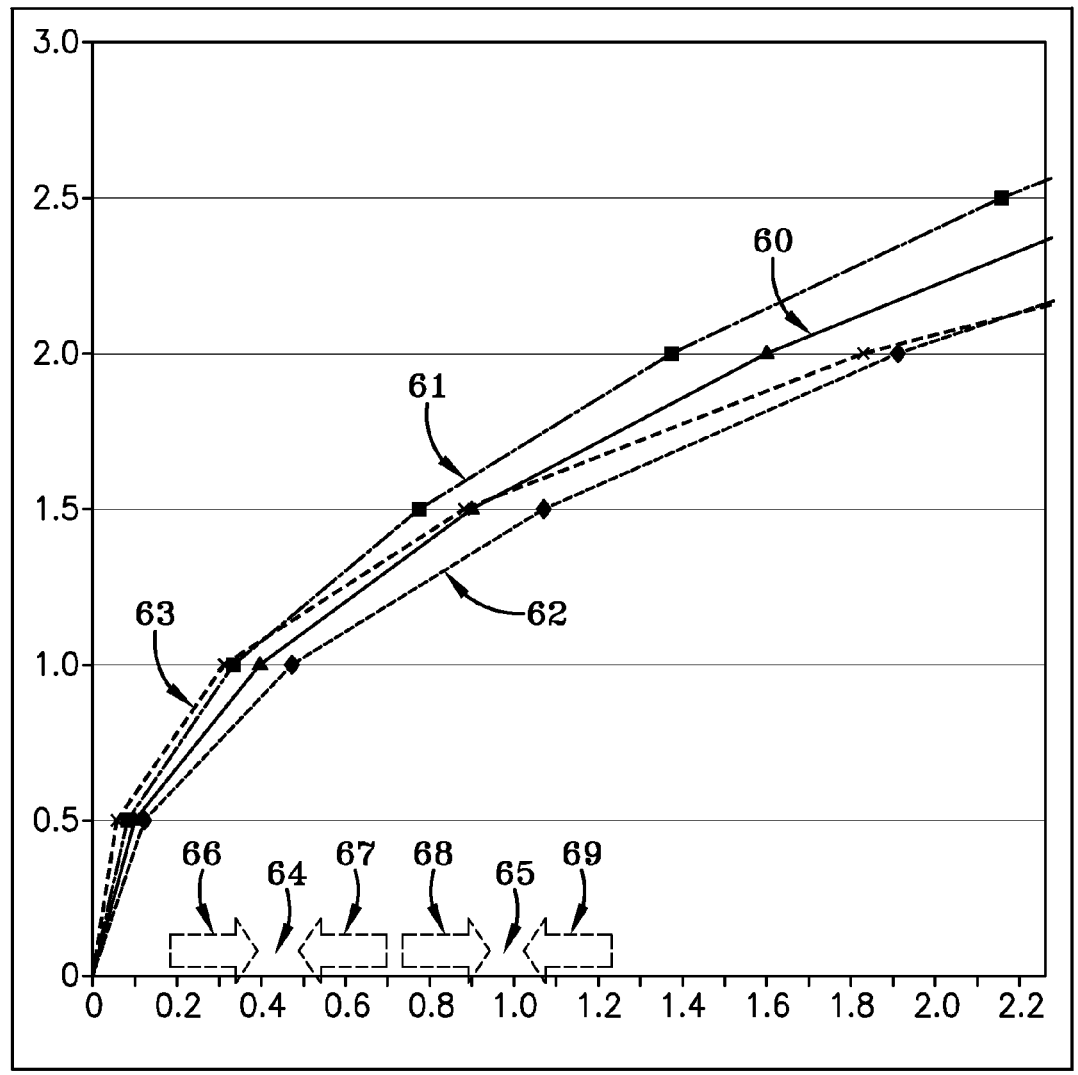
FIG. 4d is a simplified depiction of a generalized paraboloid with better focusing character than a paraboloid in which n=2. The electrode usage is shown. The generalized paraboloid, which is an interpolation (optimization) between two optimized paraboloids for a new electrode and for a used (burned down) electrode is also shown.

FIG. 4d shows sectional views of a number of paraboloids. Numeral 62 indicates a paraboloid of the shape $y^2=2px$ with $p=0.9$ as indicated by numeral 64 at the x axis which specifies the p/2 value (focal point of the paraboloid). Two electrode tips of a new electrode 66 (inner tip) and 67 (outer tip) are also shown in the Figure. If the electrodes are fired and the tips are burning down the position of the tips change, for example, to position 68 and 69 when using an electrode which adjusts its position to compensate for the tip burn down. In order to generate pressure pulse/shock waves having nearly plane characteristics, the paraboloid has to be corrected in its p value. The p value for the burned down electrode is indicate by 65 as p/2=1. This value, which constitutes a slight exaggeration, was chosen to allow for an easier interpretation of the Figure. The corresponding paraboloid has the shape indicated by 61, which is wider than paraboloid 62 because the value of p is increased. An average paraboloid is indicated by numeral 60 in which p=1.25 cm. A generalized paraboloid is indicated by dashed line 63 and constitutes a paraboloid having a shape between paraboloids 61 and 62. This particular generalized paraboloid was generated by choosing a value of n≠2 and a p value of about 1.55 cm. The generalized paraboloid compensates for different p values that result from the electrode burn down and/or adjustment of the electrode tips.

Figure 5:
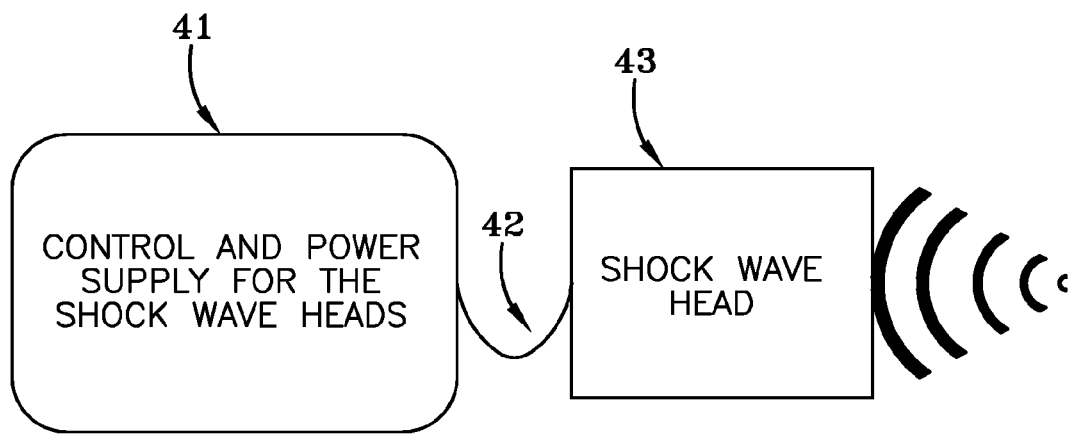
FIG. 5 is a simplified depiction of a pressure pulse/shock wave generator being connected to a control/power supply unit.

FIG. 5 is a simplified depiction of a set-up of the pressure pulse/shock wave generator 43 (shock wave head) and a control and power supply unit 41 for the shock wave head 43 connected via electrical cables 42 which may also include water hoses that can be used in the context of the present invention. However, as the person skilled in the art will appreciate, other set-ups are possible and within the scope of the present invention.

Figure 6:
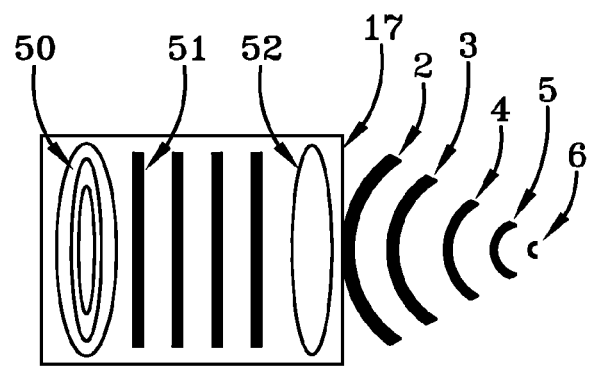
FIG. 6 is a simplified depiction of a pressure pulse/shock wave generator comprising a flat EMSE (electromagnetic shock wave emitter) coil system to generate nearly plane waves as well as an acoustic lens. Convergent wave fronts are leaving the housing via an exit window.

FIG. 6 is a simplified depiction of the pressure pulse/shock wave generator (shock wave head) having an electromagnetic flat coil 50 as the generating element. Because of the plane surface of the accelerated metal membrane of this pressure pulse/shock wave generating element, it emits nearly plane waves which are indicated by lines 51. In shock wave heads, an acoustic lens 52 is generally used to focus these waves. The shape of the lens might vary according to the sound velocity of the material it is made of. At the exit window 17 the focused waves emanate from the housing and converge towards focal point 6.

Figure 7:
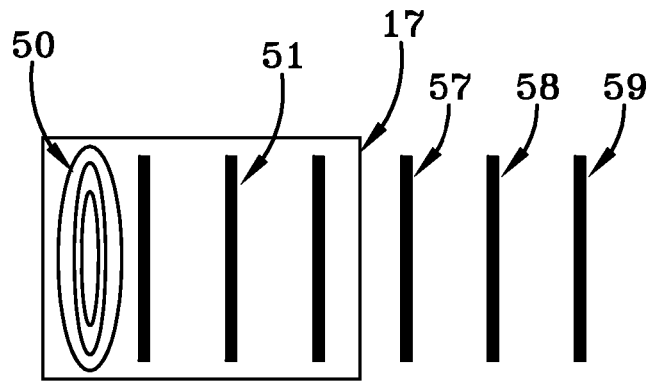
FIG. 7 is a simplified depiction of a pressure pulse/shock wave generator having a flat EMSE coil system to generate nearly plane waves. The generator has no reflecting or focusing element. As a result, the pressure pulse/shock waves are leaving the housing via the exit window unfocused having nearly plane wave characteristics.

FIG. 7 is a simplified depiction of the pressure pulse/shock wave generator (shock wave head) having an electromagnetic flat coil 50 as the generating element. Because of the plane surface of the accelerated metal membrane of this generating element, it emits nearly plane waves which are indicated by lines 51. No focusing lens or reflecting lens is used to modif the characteristics of the wave fronts of these waves, thus nearly plane waves having nearly plane characteristics are leaving the housing at exit window 17.

Figure 8:
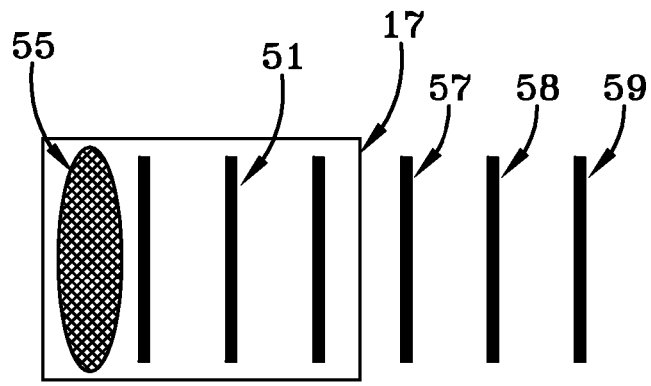
FIG. 8 is a simplified depiction of a pressure pulse/shock wave generator having a flat piezoceramic plate equipped with a single or numerous individual piezoceramic elements to generate plane waves without a reflecting or focusing element. As a result, the pressure pulse/shock waves are leaving the housing via the exit window unfocused having nearly plane wave characteristics.

FIG. 8 is a simplified depiction of the pressure pulse/shock wave generator (shock wave head) having an piezoceramic flat surface with piezo crystals 55 as the generating element. Because of the plane surface of this generating element, it emits nearly plane waves which are indicated by lines 51. No focusing lens or reflecting lens is used to modif the characteristics of the wave fronts of these waves, thus nearly plane waves are leaving the housing at exit window 17. Emitting surfaces having other shapes might be used, in particular curved emitting surfaces such as those shown in FIGS. 4a to 4c as well as spherical surfaces. To generate waves having nearly plane or divergent characteristics, additional reflecting elements or lenses might be used. The crystals might, alternatively, be stimulated via an electronic control circuit at different times, so that waves having plane or divergent wave characteristics can be formed even without additional reflecting elements or lenses.

Figure 9:
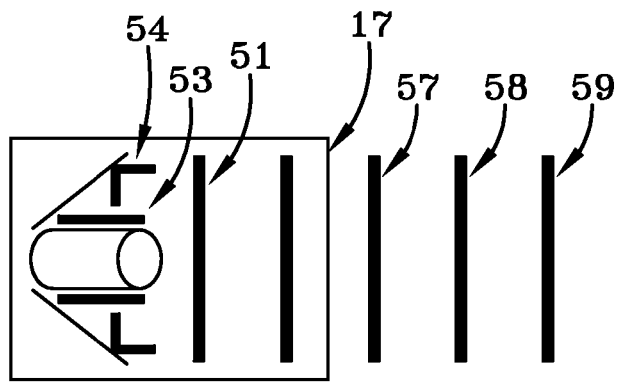
FIG. 9 is a simplified depiction of a pressure pulse/shock wave generator having a cylindrical EMSE system and a triangular shaped reflecting element to generate plane waves. As a result, the pressure pulse/shock waves are leaving the housing via the exit window unfocused having nearly plane wave characteristics.

FIG. 9 is a simplified depiction of the pressure pulse/shock wave generator (shock wave head) comprising a cylindrical electromagnet as a generating element 53 and a first reflector having a triangular shape to generate nearly plane waves 54 and 51. Other shapes of the reflector or additional lenses might be used to generate divergent waves as well.

Figure 10:
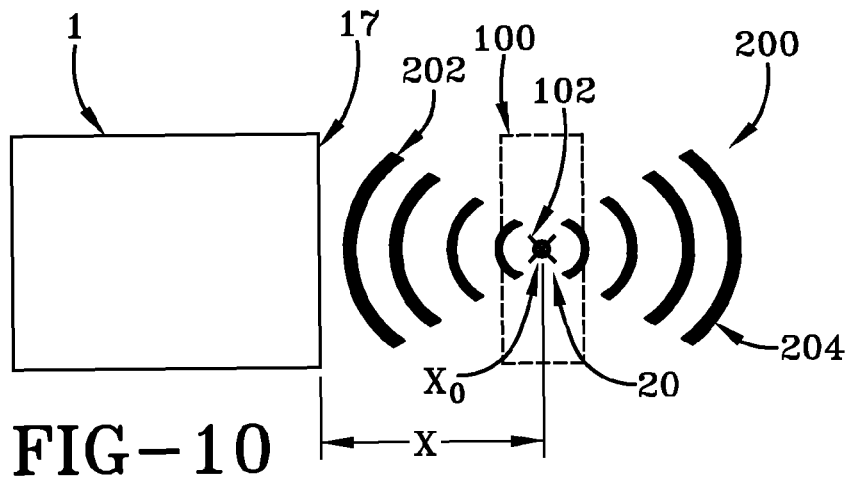
FIG. 10 is a simplified depiction of a pressure pulse/shock wave (PP/SW) generator with focusing wave characteristics shown focused with the focal point or geometrical focal volume being on a substance, the focus being targeted on the location $X_0$.
Figure 11:
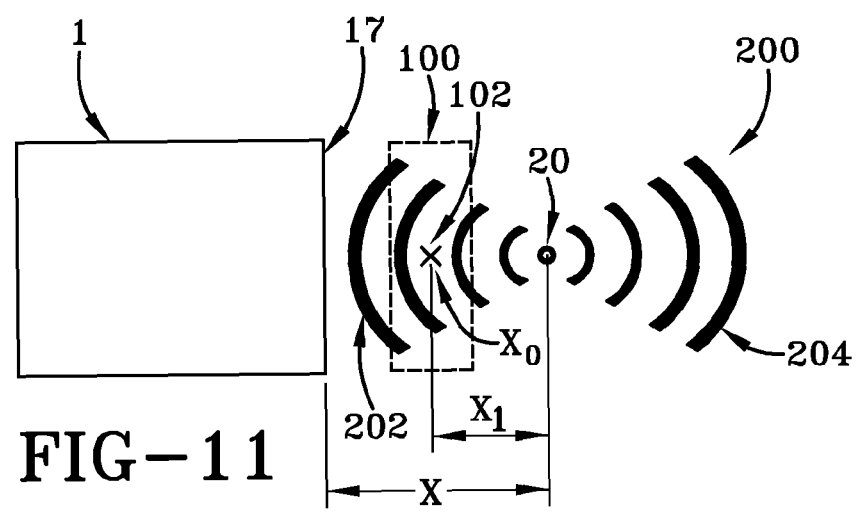
FIG. 11 is a simplified depiction of a pressure pulse/shock wave (PP/SW) generator with the focusing wave characteristics shown wherein the focus is located a distance X, from the location $X_0$ of a substance wherein the converging waves impinge the substance in a convergent off target wave front.
Figure 12:
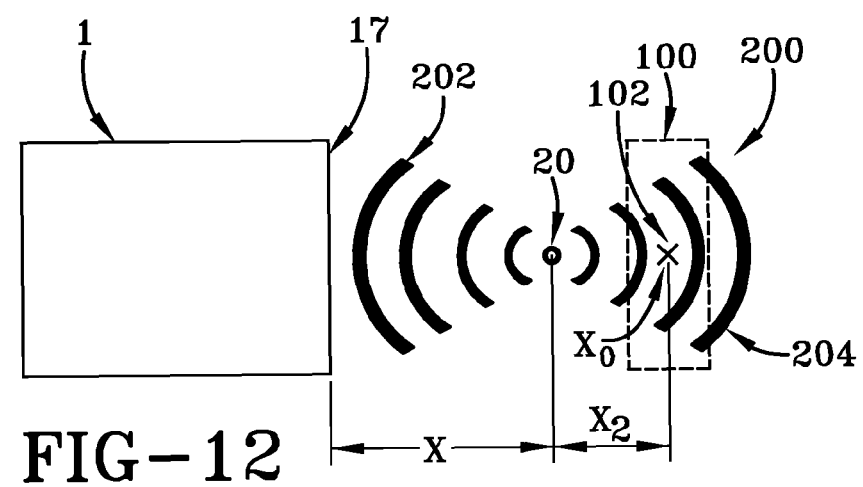
FIG. 12 is a simplified depiction of a pressure pulse/shock wave (PP/SW) generator with focusing wave characteristics shown wherein the focus is located a distance $X_2$ from the mass location $X_0$ wherein the emitted divergent waves impinge the substance.

With reference to FIGS. 10, 11 and 12 a schematic view of a shock wave generator or source 1 is shown emitting a shock wave front 200 from an exit window 17. The shock wave front 200 has converging waves 202 extending to a focal point or focal geometric volume 20 at a location spaced a distance X from the generator or source 1. Thereafter the wave front 200 passes from the focal point or geometric volume 20 in a diverging wave pattern as has been discussed in the various other FIGS. 1-9 generally.

With particular reference to figure 10 a substance 100 is shown generally centered on the focal point or volume 20 at a location $X_0$ within the substance 100. In this orientation the emitted waves are focused and thus are emitting a high intensity acoustic energy at the location $X_0$. This location $X_0$ can be anywhere within or on the substance. Assuming the substance 100 is a tissue having a mass 102 at location $X_0$ then the focus is located directly on the mass 102. In one method of treating a tumor or any other type mass 102 these focused waves can be directed to destroy or otherwise reduce the mass 102.

With reference to FIG. 11, the substance 100 is shifted a distance X toward the generator or source 1. The substance 100 at location $X_0$ being positioned a distance $X-X_1$ from the source 1. This insures the substance 100 is impinged by converging waves 202 but removed from the focal point 20. When the substance 100 is tissue this bombardment of converging waves 202 stimulates the cells activating the desired healing response as previously discussed. This is defined herein as an off target converging wave front.

With reference to FIG. 12, the substance 100 is shown shifted or located in the diverging wave portion 204 of the wave front 200. As shown $X_0$ is now at a distance $X_2$ from the focal point or geometric volume 20 located at a distance X from the source 1. Accordingly $X_0$ is located a distance $X+X_2$ from the source 1. As in FIG. 10 this region of diverging waves 204 can be used to stimulate the substance 100 which when the substance is a cellular tissue stimulates the cells to produce the desired healing effect or response.

As shown the use of these acoustic wave forms can be used separately or in combination to achieve the desired therapeutic effect.

Furthermore such acoustic wave forms can be used in combination with drugs, chemical treatments, irradiation therapy or even physical therapy and when so combined the stimulated cells will more rapidly assist the body's natural healing response.

The present invention provides an apparatus for an effective treatment of indications, which benefit from low energy pressure pulse/shock waves having nearly plane or even divergent characteristics. For the treatment of those indications, the procedure to locate the area to which the pressure pulses/shock waves are applied often needs to be less accurate than, e.g., when kidney stones are destroyed with focused waves. In fact, sometimes the knowledge of the physique of the subject to be treated is sufficient, so that imaging devices like ultrasound, x-ray or similar, as they are known from devices used in the destruction of kidney stones, are not required. For certain indication, it might be advantageous to a treat an entire area simultaneously, for example if the affected tissue is spread out and has a more area like character rather than a volume like character. One example of such an indication is spread out muscle pain. The small focal points/focus volumes (defined as −6 dB of the maximum pressure amplitude at a certain energy output setting) of a few mm (for example 2-25 mm) produced by focused waves might be too small to optimally treat the affected area. The area of the focal point/focus volume can be enlarged by reducing the focusing or even by eliminating it all together by using an apparatus according to the present invention which produces waves having wave fronts with nearly plane or divergent characteristics.

With an unfocused wave having plane, nearly plane wave characteristic, convergent off target or even divergent wave characteristics, the energy density of the wave may be or may be adjusted to be so low that side effects including pain are very minor or even do not exist at all.

In certain embodiments, the apparatus of the present invention is able to produce waves having energy density values that are below 0.1 mJ/mm2 or even as low as 0.000 001 mJ/mm2. In a preferred embodiment, those low end values range between 0.1-0.001 mJ/mm2. With these low energy densities, side effects are reduced and the dose application is much more uniform. Additionally, the possibility of harming surface tissue is reduced when using an apparatus of the present invention that generates waves having nearly plane or divergent characteristics and larger transmission areas compared to apparatuses using a focused shock wave source that need to be moved around to cover the affected area. The apparatus of the present invention also may allow the user to make more precise energy density adjustments than an apparatus generating only focused shock waves, which is generally limited in terms of lowering the energy output.

The treatment of the above mentioned indications are believed to be a first time use of acoustic shock wave therapy generally with the exception of the heart and pancreas which have been subjected to tissue focal point targeted by focused shock waves. None of the work done to date has treated the above mentioned indications with convergent, divergent, planar or near-planar acoustic shock waves of low energy. Accordingly the use of acoustic shock waves for treating such indications as cirrhosis of the liver, cancer, myelodysplasia, stomach ulcers, AIDs, Alzheimer's disease, bone cancer, arthritis, emphysema, gout, rheumatic disease, HIV, leprosy, lupus, skin sarcomas, cellulitis, melanomas, osteoporosis, periodontal diseases, pseudoarthrosis, wounds, scars, acne, burns, diabetes, cystic fibrosis, nerve paraplegia or enhancing stem cell reactions are completely new and a breakthrough in medical treatments of such diseases. As is the use of acoustic shock waves for germicidal wound cleaning or preventive medical treatments.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

We claim:

1. A therapeutic shock wave device for treating living tissue to produce a living tissue reaction in a subject to which the shock wave is administered comprising: a reflector housing; a parabolic reflector disposed in the housing; and an energy source disposed within the parabolic reflector for developing a shock wave so that a planar shock wave is formed by the parabolic reflector and emanates from the housing and is transferred to the living tissue; in the absence of a focusing lens through an exit window or membrane coupled to the tissue so that the emitted wave is transmitted unfocused from the exit window or membrane to the treated living tissue with reflected unfocused flat acoustic waves wherein the parabolic reflector is shaped and dimensioned to provide the planar shock wave having a power density level to produce a tissue reaction in a subject to which the wave is administered and wherein the shock wave has a power density in the range of approximately 0.01 mJ/mm$^2$ up to 1.0 mJ/mm$^2$ to stimulate the treated living tissue while avoiding tissue damage.

2. The device of claim 1, and further comprising a coupling member which intersects the reflector along a circle having a diameter in the range of approximately 20 mm to 100 mm.

3. The device of claim 1 wherein the parabolic reflector has an origin point and a focal point spaced from the origin point a distance in the range of approximately 3 mm to 10 mm.

4. The device of claim 1 wherein the energy source is an electrohydraulic source.

5. The device of claim 1 wherein the energy source has a propagation point centered approximately at a focal point of the parabolic reflector.

6. The device of claim 1 wherein the energy source comprises a pair of electrode tips connected to a capacitor.

7. The device of claim 6 wherein the energy source has a propagation point centered approximately between the electrode tips.

8. The device of claim 1 wherein the parabolic reflector includes a cavity having an opening and the opening sealed by a membrane.

9. The device of claim 8 wherein the cavity contains a fluid.

10. The device of claim 9 wherein the fluid is water.

* * * * *